「 
US011357637B2

(12) United States Patent
Harris, Jr.

(10) Patent No.: US 11,357,637 B2
(45) Date of Patent: Jun. 14, 2022

(54) FIXATION MECHANISM FOR AN IMPLANT

(71) Applicant: Wright Medical Technology, Inc., Memphis, TN (US)

(72) Inventor: Brian R. Harris, Jr., Cordova, TN (US)

(73) Assignee: WRIGHT MEDICAL TECHNOLOGY, INC., Memphis, TN (US)

(*) Notice: Subject to any disclaimer, the term of this patent is extended or adjusted under 35 U.S.C. 154(b) by 0 days.

(21) Appl. No.: 16/583,327

(22) Filed: Sep. 26, 2019

(65) Prior Publication Data

US 2020/0015978 A1   Jan. 16, 2020

Related U.S. Application Data

(63) Continuation of application No. 15/540,093, filed as application No. PCT/US2016/012314 on Jan. 6, 2016, now Pat. No. 10,456,265.
(Continued)

(51) Int. Cl.
*A61F 2/44* (2006.01)
*A61F 2/42* (2006.01)
(Continued)

(52) U.S. Cl.
CPC ........ *A61F 2/4202* (2013.01); *A61F 2/30749* (2013.01); *A61F 2/46* (2013.01);
(Continued)

(58) Field of Classification Search
CPC ...... A61F 2/30942; A61F 2/4202; A61F 2/30; A61F 2002/4205; A61F 2/28; A61F 2002/30677; A61F 2/389; A61F 2/66; A61F 2/6607; A61B 17/1757; A61B 2017/00477; A61B 17/0401; A61B 17/1664; A61B 17/68; A61B 2017/00004; A61B 2017/0256; A61B 17/844
See application file for complete search history.

(56) References Cited

U.S. PATENT DOCUMENTS 4,236,512 A * 12/1980 Aginsky .............. A61B 17/746
606/68
4,301,552 A    11/1981 London
(Continued)

FOREIGN PATENT DOCUMENTS

WO    2009/143057 A2    11/2009

OTHER PUBLICATIONS

International Search Report and Written Opinion issued for corresponding International patent application No. PCT/US2016/012314, dated Apr. 18, 2016, 12 pages.
(Continued)

*Primary Examiner* — Ann Schillinger
(74) *Attorney, Agent, or Firm* — Duane Morris LLP

(57) ABSTRACT

An ankle prosthesis has a tibial component configured for attachment to a tibia of a person, and a talar component. The talar component has a first surface configured for facing the tibial component and a second surface configured for facing a talus of the person. The second surface has first and second arms attached to it, for pivoting or flexing outwardly in medial and lateral directions, respectively, to engage side surfaces of a previously formed slot in the talus.

6 Claims, 10 Drawing Sheets

Related U.S. Application Data

(60) Provisional application No. 62/100,695, filed on Jan. 7, 2015.

(51) Int. Cl.
*A61F 2/30* (2006.01)
*A61F 2/46* (2006.01)
*A61B 17/70* (2006.01)

(52) U.S. Cl.
CPC ........... *A61F 2002/30387* (2013.01); *A61F 2002/30433* (2013.01); *A61F 2002/30507* (2013.01); *A61F 2002/30579* (2013.01); *A61F 2002/30841* (2013.01); *A61F 2002/30878* (2013.01); *A61F 2002/30883* (2013.01); *A61F 2002/30884* (2013.01); *A61F 2002/4207* (2013.01)

(56) References Cited

U.S. PATENT DOCUMENTS

| | | | |
|---|---|---|---|
| 5,062,851 A | | 11/1991 | Branemark |
| 5,882,351 A | * | 3/1999 | Fox ........................ A61B 17/88 606/908 |
| 6,126,692 A | | 10/2000 | Robie et al. |
| 7,909,825 B2 | * | 3/2011 | Saravia ............... A61B 17/7266 606/66 |
| 8,808,303 B2 | | 8/2014 | Stemniski et al. |
| 9,155,574 B2 | * | 10/2015 | Saravia ............... A61B 17/1725 |
| 9,480,511 B2 | | 11/2016 | Butters et al. |
| 2003/0040810 A1 | | 2/2003 | Molino et al. |
| 2004/0167631 A1 | | 8/2004 | Luchesi et al. |
| 2005/0288792 A1 | | 12/2005 | Landes et al. |
| 2008/0208349 A1 | | 8/2008 | Graser |
| 2011/0071579 A1 | * | 3/2011 | Reach, Jr. .......... A61B 17/0401 606/327 |
| 2011/0166608 A1 | * | 7/2011 | Duggal .............. A61B 17/7291 606/328 |
| 2012/0172934 A1 | * | 7/2012 | Fisher ................ A61B 17/8841 606/304 |
| 2013/0131822 A1 | * | 5/2013 | Lewis ................ A61B 17/7266 623/21.19 |
| 2014/0135939 A1 | | 5/2014 | Petteys |
| 2014/0296995 A1 | | 10/2014 | Reiley et al. |
| 2016/0038299 A1 | | 2/2016 | Chen et al. |

OTHER PUBLICATIONS

Examination Report No. 1 issued in connection with corresponding Australian patent application No. 2016205292, dated Feb. 27, 2018, 9 pages.

Examination Report No. 2 issued in connection with corresponding Australian patent application No. 2016205292, dated Jul. 12, 2018, 5 pages.

Supplementary Partial European Search Report issued in connection with European Patent Application No. 16735347.3, dated Oct. 26, 2018, 6 pages.

Office Action issued in corresponding Canadian Patent Application No. 3,042,891, dated Oct. 13, 2020, 4 pages.

* cited by examiner

FIXATION MECHANISM FOR AN IMPLANT

CROSS-REFERENCE TO RELATED APPLICATIONS

This application is a continuation of U.S. patent application Ser. No. 15/540,093, filed on Jun. 27, 2017, which is a National Stage Application, filed under 35 U.S.C. 371, of International Patent Application No. PCT/US2016/012314, filed on Jan. 6, 2016 which claims priority to U.S. Provisional Patent Application No. 62/100,695, filed Jan. 7, 2015, the entireties of which are incorporated by reference herein.

FIELD

This disclosure relates to medical devices generally, and more specifically to an implant suitable for attachment to at least one bone.

BACKGROUND

Numerous ankle joint replacement prostheses have been developed.

U.S. Patent Application Publication No. 2014/0135939, assigned to the assignee of the present patent application, discloses an ankle prosthesis comprising: a tibial component configured for attachment to a tibia, and a talar component configured for attachment to a talus. The tibial component comprises an attachment surface on a proximal portion and an articulation surface on a distal portion. The talar component comprises an attachment surface on a distal portion and an articulation surface on a proximal portion. The articulation surface of the tibial component comprises at least one convex contour on a medial portion and at least one convex contour on a lateral portion. The articulation surface of the talar component comprises at least one concave contour on a medial portion and at least one concave contour on a lateral portion, configured to compliment the articulation surface of the tibial component. The articulation surface of the talar component comprises a lip configured to maintain congruence of the articulation surface of the tibial component with the articulation surface of the talar component.

The talar component is attached to the talus by one or more screws or one or more rods.

SUMMARY

In some embodiments, an ankle prosthesis comprises a tibial component configured for attachment to a tibia of a person, and a talar component. The talar component has a first surface configured for facing the tibial component and a second surface configured for facing a talus of the person. The second surface has first and second arms attached thereto, for pivoting or flexing outwardly in medial and lateral directions, respectively, to engage side surfaces of a previously formed slot in the talus.

In some embodiments, a prosthesis comprises a first component configured for attachment to a first bone of a person, the first component having an articulating surface. A second component has an articulating surface configured for facing the articulating surface of the first component, the second component has a second surface configured for facing a second bone of the person. The second surface has first and second arms attached thereto, for pivoting or flexing outwardly in medial and lateral directions, respectively, to engage side surfaces of a previously formed slot in the second bone.

In some embodiments, a method of fixing an implant component to a bone, comprises: forming a slot in the bone, the slot having side edges; positioning the implant component adjacent the bone, so that first and second arms of the implant component fit within the slot; and pivoting or flexing the first and second arms towards respective side edges of the slot.

DETAILED DESCRIPTION

Figure 1:
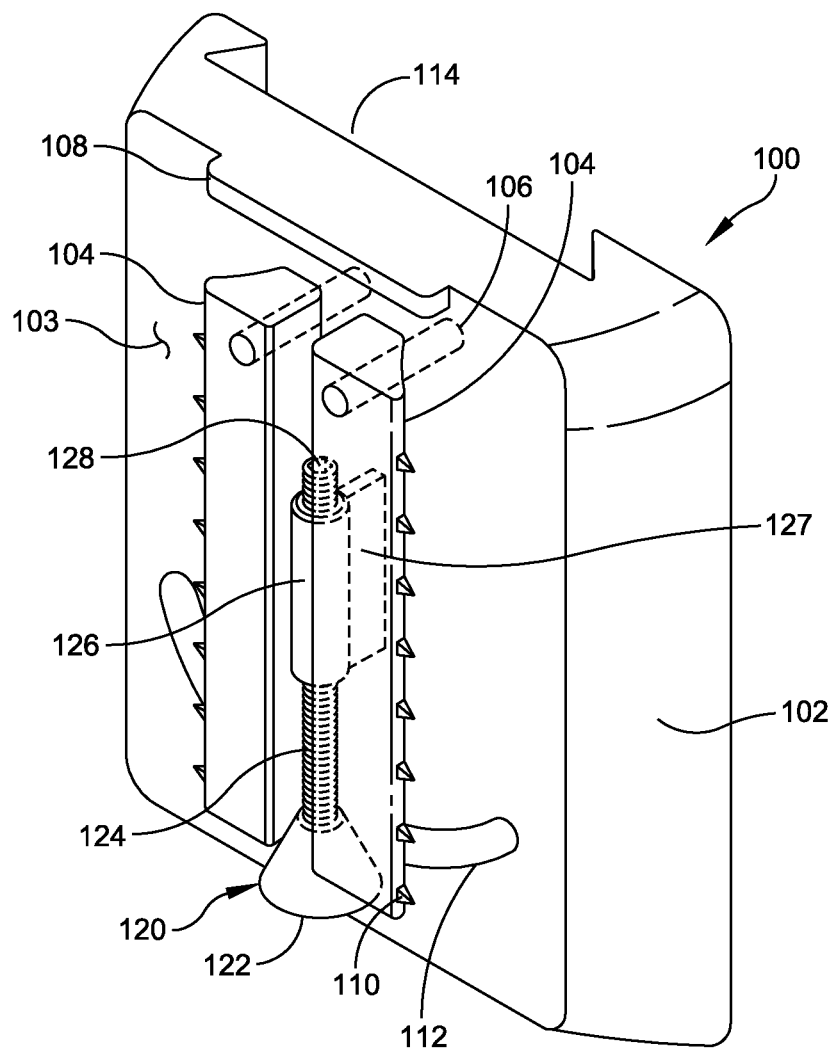
FIG. 1 is an isometric view of an exemplary attachment plate suitable for inclusion in a talar component of an ankle prosthesis according to some embodiments.

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

This disclosure provides an ankle prosthesis having an attachment plate for fixing the talar component of the prosthesis to bone. The attachment plate can provide stability, even in the case of compromised soft tissue or bone. Depending on the condition of the patient's bones, the attachment plate can be used to grip cancellous bone, the posterior cortical wall, or both. In some patients, the plate may be used to grip the medial and lateral cortices.

Figure 2:
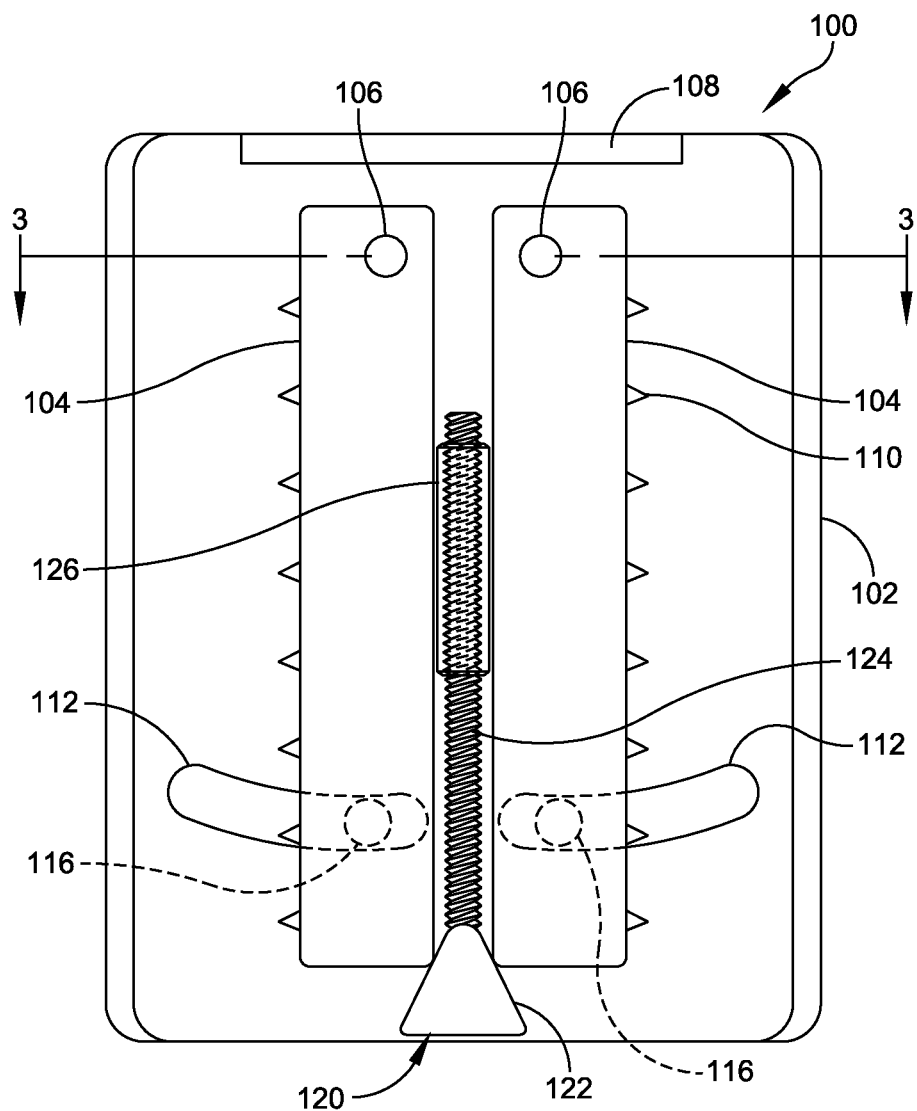
FIG. 2 is a distal (bottom) plan view of the attachment plate of FIG. 1.
Figure 3:
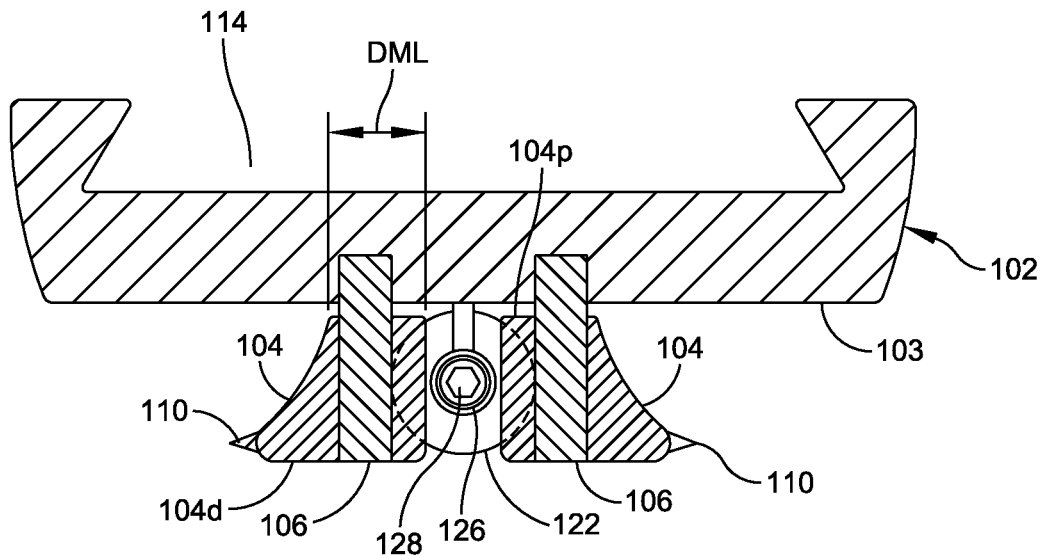
FIG. 3 is a cross-sectional view taken along section line 3-3 of FIG. 2.
Figure 4:
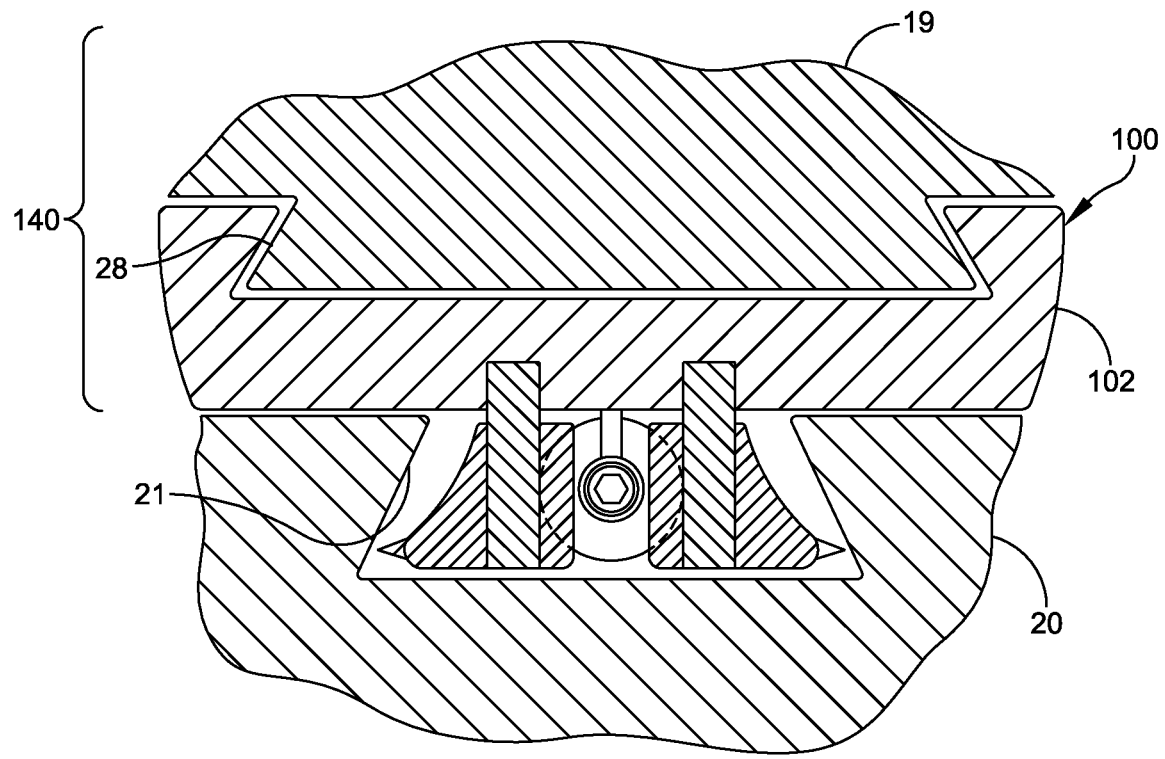
FIG. 4 is a cross section of the talar component including the attachment plate of FIG. 1.
Figure 7:
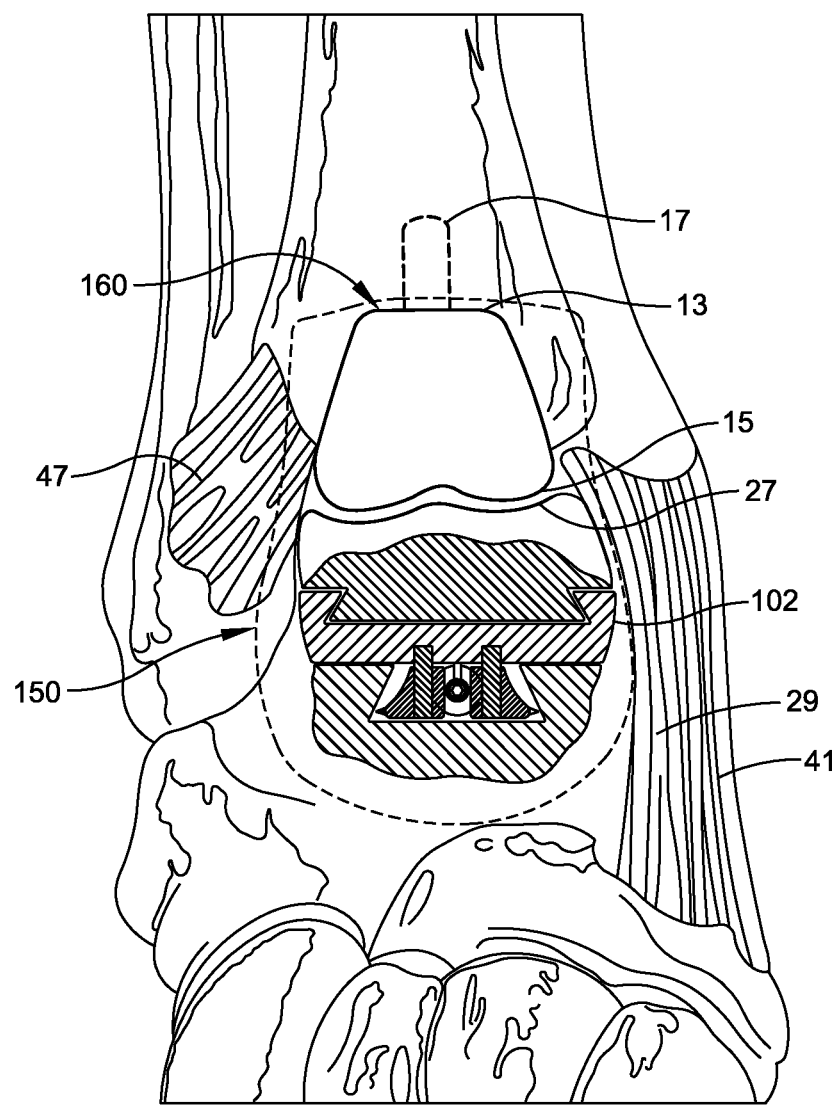
FIG. 7 is an anterior view of tibia and talus with the implanted prosthesis including the distal plate portion of FIG. 1.

FIG. 1 is an isometric view of an exemplary attachment plate 100 suitable for inclusion in a talar component 140 (FIG. 4) of an ankle prosthesis 150 (FIG. 7) according to some embodiments of this disclosure. FIG. 2 is a distal (bottom) plan view of the attachment plate 100. FIG. 3 is a cross-sectional view taken along section line 3-3 of FIG. 2. FIG. 4 is a cross section of the talar component 140 including the attachment plate 100.

The ankle prosthesis 150 comprises a tibial component 160 (FIG. 7) configured for attachment to a tibia of a person, and a talar component 140 configured for attachment to the talus 20. In some embodiments, the talar component 140 approximates the natural anatomy of the talus bone and the tibial component comprises a complementary contour. In other embodiments, the natural anatomy is mimicked in a reverse orientation, such that the tibial component 160 has a bicondylar contour and a talar component 140 has a complementary contour. The tibial component 160 has an attachment surface 13 and an articulating surface 15.

In some embodiments, the tibial component 160 is a unitary body formed of a single piece of material, such as titanium alloy, cobalt-chrome alloy, chrome-titanium alloy or stainless steel. In other embodiments (not shown), the attachment surface 13 is formed on a proximal portion suitable for permanent insertion and formed of a material such as titanium alloy, cobalt-chrome alloy, chrome-titanium alloy or stainless steel, and the articulating surface 15 is formed on a distal portion which is a detachable and replaceable insert mounted to the proximal portion. The distal portion can be made of a different material from the proximal portion. For example, the distal portion can be made of a polymer material, such as ultra-high molecular weight polyethylene (UHMWPE).

In some embodiments, the tibial component 160 is affixed to the distal end of the tibial bone by a stem 17, which can be a unitary stem or a modular stem (not shown) comprising two or more stem sections. In other embodiments (not shown), the tibial component has a pair of expandable arms similar to the arms 104 of the tibial component 160 described below.

A talar component 140 has a first surface (an articulating surface) 27 configured for facing the tibial component 160 and a second surface (an attachment surface) 103 configured for facing a talus 20 of the person. The second surface 103 has first and second arms 104 attached thereto, for pivoting or flexing outwardly in medial and lateral directions 132, 133 (FIG. 5), respectively, to engage side surfaces of a previously formed slot 21 (FIGS. 4 and 10) in the talus 20.

In some embodiments, each of the arms 104 is pivotally attached to the second (attachment) surface 103 of the talar component 140 by a pin 106. The arms 104 can be pivoted by a driving mechanism (described below) to grip cancellous bone, the posterior cortical wall, and/or medial and lateral cortical walls.

In some embodiments, the second (attachment) surface 103 is included in a distal plate portion 102 having first and second guide slots 112, and each of the arms 104 has a pin 116 extending from the arm. The pin 116 is movable within the guide slot 112 during pivoting or flexing of the arms 104.

Figure 5:
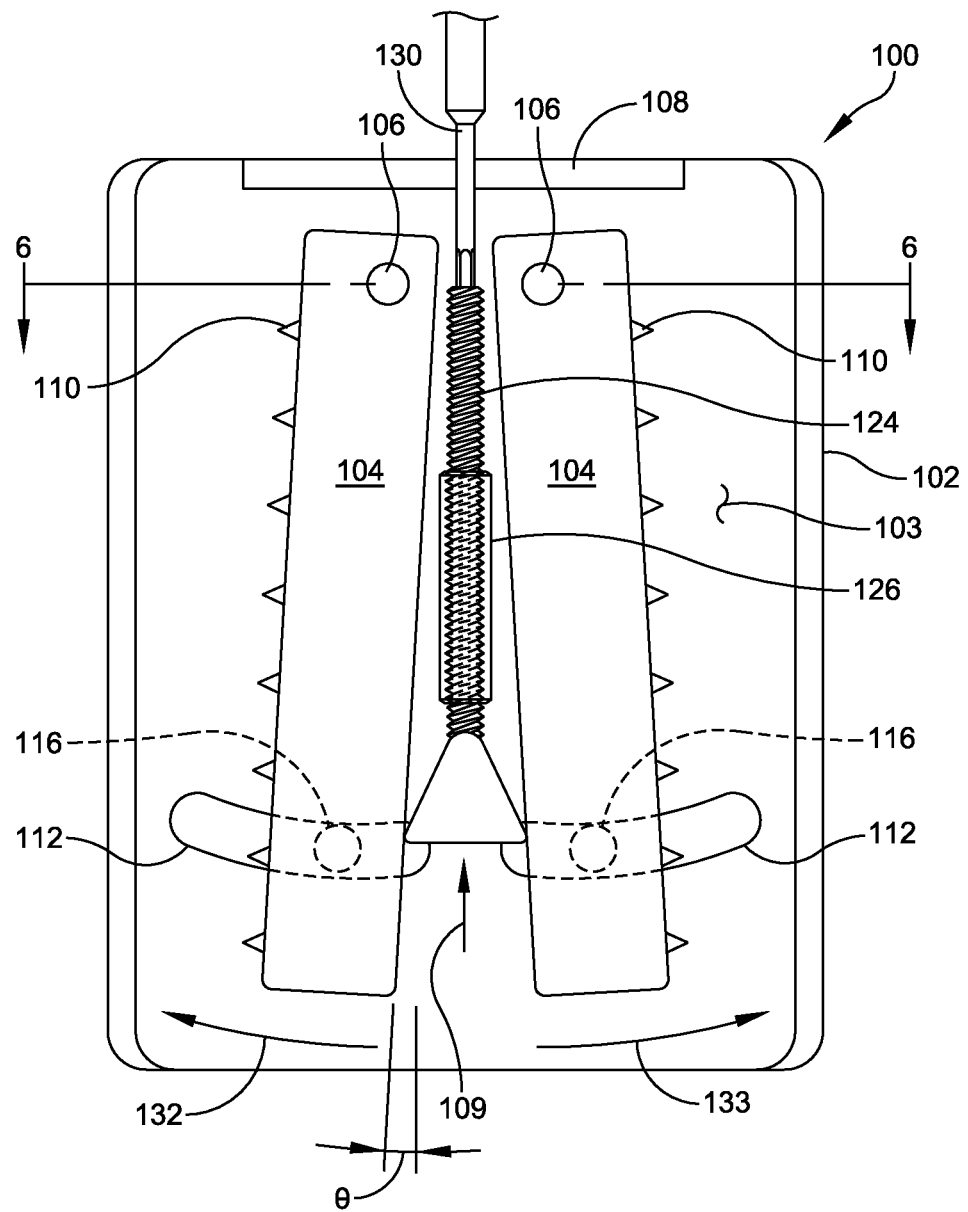
FIG. 5 is a distal (bottom) plan view of the attachment plate of FIG. 2, with its arms rotated.

In some embodiments, a driving mechanism 120 includes a separator 122 positioned between the first and second arms 104. The separator 122 is configured to be advanced towards an anterior end of each of the first and second arms 104 attached to the second (attachment) surface 103, for causing the first and second arms 104 to pivot or flex outwardly, in the medial and lateral directions 132, 133, as best seen in FIG. 5. In some embodiments, the separator 122 is a cone or wedge.

In some embodiments, the separator 122 is attached to a threaded member 124 for moving the separator in an anterior-posterior direction. For example, as shown in FIGS. 1, 2 and 5, an end of the threaded member 124 can be fixedly attached to the separator 122. In some embodiments, the attachment is by engagement between the threaded member 124 and a female thread (not shown) in separator 122. In other embodiments, the threaded member 124 and separator 122 are two sections of a single unitary piece formed (e.g., by casting) from a single material. In other embodiments, the threaded member 124 can have an end interference-fitted to the separator 122.

The threaded member 124 is threadably received by a female socket 126 fixedly attached to the second (attachment) surface 103. In some embodiments, the female socket 126 is formed from the same piece of material as the distal plate portion 102 and is spaced apart from the plate portion 102 by a rib or support member 127. The threaded member 124 has a socket 128 or slot (not shown) at the anterior end of the threaded member 124. The surgeon can rotate the threaded member 124 using a tool 130 (FIG. 5) having a tip configured to be received by the socket 128 or slot (not shown). When the surgeon rotates the threaded member 124, the threaded member moves along the anterior-posterior axis 109 of the implant 150. When the threaded member 124 moves in the anterior direction, the separator 122 also moves in the anterior direction, causing the posterior ends of the arms 104 to pivot outward in the medial and lateral directions 132, 133. (If the distal plate portion 102 is attached to the left talus, direction 132 is medial and direction 133 is lateral. If the distal plate portion 102 is attached the right tibia, direction 132 is lateral and direction 133 is medial.)

In other embodiments (not shown), the separator 122 is a wedge having straight sides that are engaged by the medial sides of the arms 104, preventing the wedge from rotating. The threaded member 124 is threadably received by the wedge, and can rotate relative to the wedge, causing the wedge 122 to advance or retract along the threaded member in the anterior-posterior direction 109. The threaded member 124 can be mounted to permit rotation, but not linear travel. For example, the threaded member can have a smooth section (not shown) that serves as a journal of a journal bearing. The female socket 126 is replaced by a smooth socket or bearing (not shown) that receives the smooth section of the threaded member 124. The result of rotating the threaded member is the same as described above; the separator 122 advances, causing the posterior ends of the arms 104 to separate from each other in the medial-lateral direction 132, 133.

Figure 6:
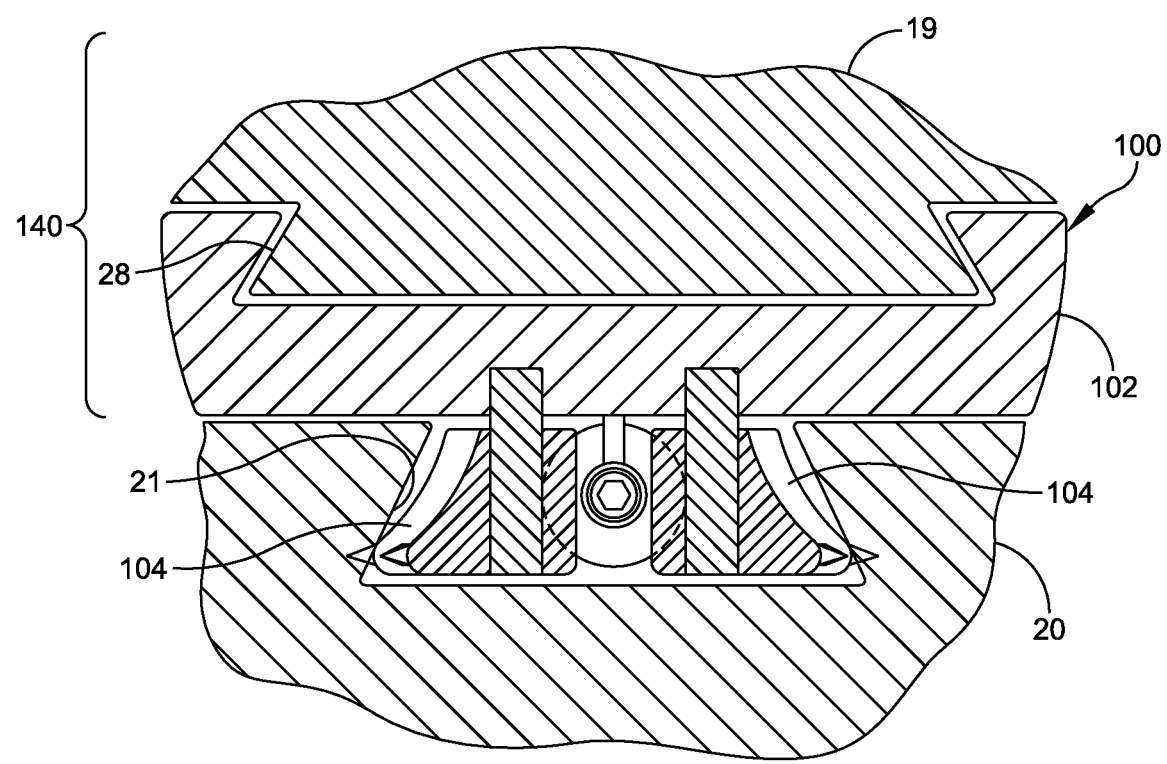
FIG. 6 is a cross-sectional view taken along section line 6-6 of FIG. 5.

FIG. 6 is a cross-sectional view of the talar component 140 after the arms 104 are pivoted outwardly in the medial and lateral directions. Compared to the cross-sectional views in FIGS. 3 and 4 (prior to pivoting the arms 104), FIG. 6 shows the rear of each arm 104 extending outwardly to grip the medial and lateral sides of the slot 21.

In some embodiments, each of the arms 104 has a plurality of barbs 110 on an outer (medial or lateral) edge of the arm. The barbs 110 can grip cancellous bone or the cortical walls of the bone.

In some embodiments, the slot 21 is formed in the talus 20 with undercut side surfaces, in a trapezoidal or dove-tail shape, and the arms 104 have a medial-lateral dimension DML (FIG. 3) that increases from a proximal side 104p of each arm 104 adjacent the second surface 103 to a distal side 104d of each arm 104 configured to face the talus 20. In some embodiments, each arm 104 has an approximately trapezoidal cross section, as shown in FIGS. 3, 4 and 6. The two arms 104 having approximately trapezoidal cross sections are adapted to be received in the dove-tail shaped slot 21 in the talus 20. The outer sides of the arms 104 bear against the side walls of the slot 21. The wider distal sides 104d of the arms extend under the undercut side walls of the slot 21, resisting pullout.

In some embodiments, the distal plate portion 102 has an anterior lip 108. The implant 150 is configured to be inserted from an anterior side. The anterior lip 108 provides a positive stop that bears against the anterior cortical wall of the talus when the distal plate portion 102 is inserted in the posterior direction. When the arms 104 pivot outwardly, the outside of each arm applies a force in an oblique direction. The force has a component in the medial-lateral direction and a component in the anterior direction. As the angle θ (FIG. 5) of the pivoting increases, the anterior component of the force applied by each arm also increases. The anterior component of the force is approximately proportional to the sine of the pivot angle θ. This anterior component of the force is met by an equal and opposite posterior force between the anterior lip 108 and the anterior cortical wall. Thus, the plate portion 102 provides additional clamping forces in the anterior-posterior direction. In some embodiments, the anterior lip 108 has an aperture (not shown) to permit access to the socket 128 of the threaded member through the aperture while the anterior lip abuts the talar bone 20.

In some embodiments, the talar component 140 comprises a proximal portion 19 and a distal plate portion 102 made of different materials from each other. For example, the proximal portion 19 having the articulating surface 27 can be a replaceable component made of a material such as UHMWPE. The distal plate portion 102 can be made of a material such as titanium alloy, cobalt-chrome alloy, chrome-titanium alloy or stainless steel or the like, for permanent implantation. In some embodiments, as shown in FIG. 4, the distal plate portion 102 has a dovetail-shaped slot 114 for receiving a trapezoidal member 28 of the proximal portion 19, forming a dovetail joint between the proximal portion 19 and the distal plate portion 102. This allows replacement of the proximal portion 19 having the articulating surface 27 (e.g., following wear of the articulating surface 27, or to make an adjustment) through the anterior side of the patient's ankle.

In some embodiments, the bottom surface of the implant 150 or arms 104 are coated to enhance biologic fixation (e.g., porous coated or plasma sprayed).

To insert the implant, the surgeon fixes the patient's foot in a suitable foot holder, and supports the posterior side of the calf. The surgeon makes an incision on the anterior side and performs soft tissue and ligament release as appropriate. The tibia and calcaneus are fixed using rods and/or wires. Approximately 6-8 mm is cut from the proximal end of the talus, providing a flat surface for attaching the talar component 140. The distal end of the tibia is cut to provide a receptacle for the proximal end 13 of the tibial component 160. A hole is drilled in the cut surface to receive the tibial stem 17 of the tibial component 160.

Figure 10:
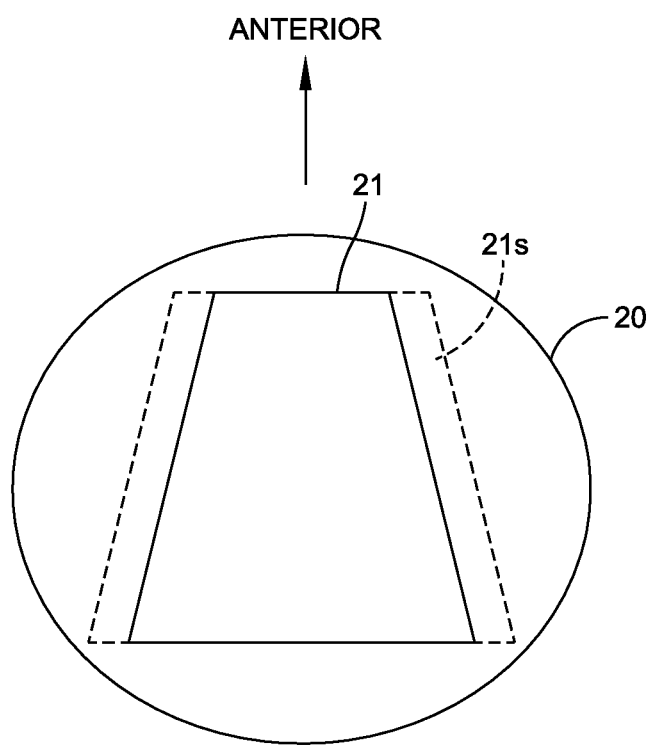
FIG. 10 shows the slot of FIG. 4, as viewed from a proximal vantage point.

The surgeon forms the slot 21 (as shown in FIG. 10) in the resectioned proximal surface of the talus 20. The slot 21 can be formed using a three-sided punch, a saw with a guide having three slots, or a dovetail styled end mill. The side walls 21s of the slot 21 are undercut, as shown in FIG. 4, so as the arms 104 are actuated outwardly, the plate portion 102 is drawn down onto the resected surface of the talus 20. In addition, the side walls 21s of the slot 21 are not parallel to each other. As best seen in FIG. 10, the slot 21 has the general shape of an isosceles trapezoid when viewed from a vantage point that is proximal relative to the talus 20. The posterior side (based) of the slot 21 is wider than the anterior side, to prevent the plate portion 102 from translating back in the anterior direction once the arms 104 are driven apart by the driving mechanism. This trapezoidal shape provides room for the arms 104 to pivot or flex outwardly before engaging the side walls 21s of the slot 21. The side walls 21s of the slot 21 are symmetrical about the anterior-posterior axis 109.

In some embodiments, the surgeon removes a small amount of the bone on the anterior side, to receive the anterior lip 108, so that the anterior lip seats flush with the bone. In other embodiments, the anterior lip 108 seats outside of the bone.

Figure 11C:
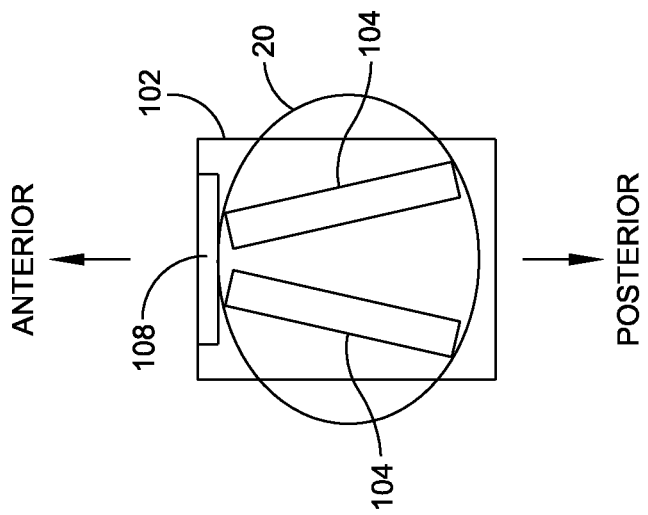
FIGS. 11A to 11C schematically show three alternative mountings of the arms relative to the cortical bone.

Depending on the quality of the talar bone, the slot 21 can be positioned in different locations relative to the cortical walls, and the length and pivot angle θ of the arms 104 correspondingly adjusted. For example, FIG. 11A shows the distal plate portion 102 positioned so that the arms 104 are completely surrounded by cancellous bone, and do not touch the cortical walls. A corresponding slot 21 is formed in the talus 20. (The size of the plate portion 102 is exaggerated for ease of viewing, but in practice the corners of the plate portion 102 will not stick out from the talus as shown in FIG. 11A.) A configuration in which the arms 104 only contact cancellous bone may be suitable if the cancellous bone is of good quality (i.e., not excessively soft or diseased).

Figure 11B:
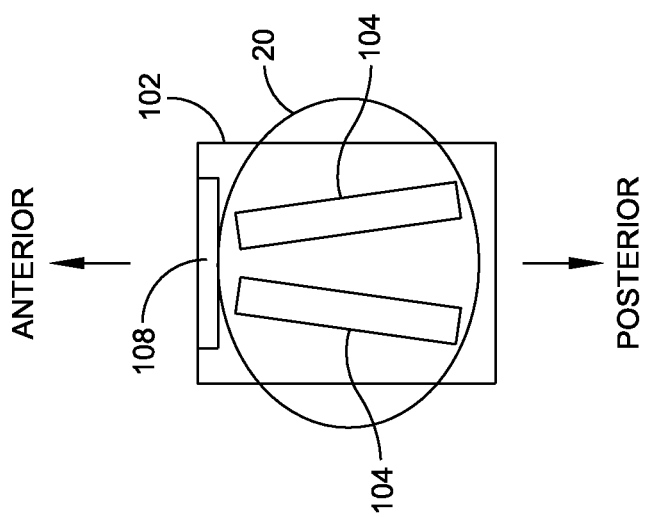
Figure 11A:
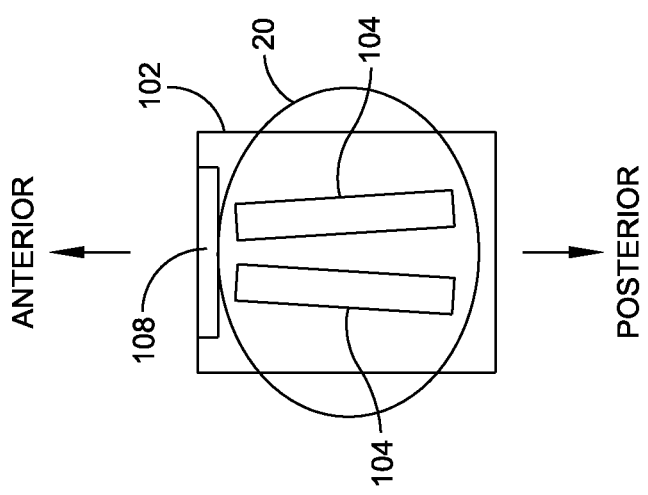

FIG. 11B shows another configuration in which the length of the arms 104 and the excursion (i.e., pivot angle θ of the arms 104) are selected so that the posterior ends of the arms 104 abut the posterior cortical wall for greater stabilization. A corresponding slot 21 is formed in the talus 20. Such a configuration may be used when the cancellous bone is of lower quality.

FIG. 11C shows another configuration in which the length of the arms 104 and the excursion (i.e., pivot angle θ of the arms 104) are selected so that the anterior and posterior ends of the arms 104 abut the anterior and posterior cortical walls, respectively, for still greater stabilization. A corresponding slot 21 is formed in the talus 20.

The tibial stem 17 and the tibial component 160 are installed. Then the distal plate portion 102 of the talar component 140 is inserted into the incision until the anterior lip 108 abuts the anterior cortical wall of the talus 20. The talar component 140 is positioned adjacent the bone 20, so that first and second arms 104 of the talar component fit within the slot 21.

The two arms 104 are seated in the slot 21, and the surgeon uses the tool 130 to rotate the threaded member 124, to advance the separator 122 in the anterior direction. The advancing of the separator causes the two arms 104 to pivot outwardly about the pins 106 to expand in the medial and lateral directions. The surgeon continues to advance the separator until the arms 104 grip the bone 20.

Figure 8:
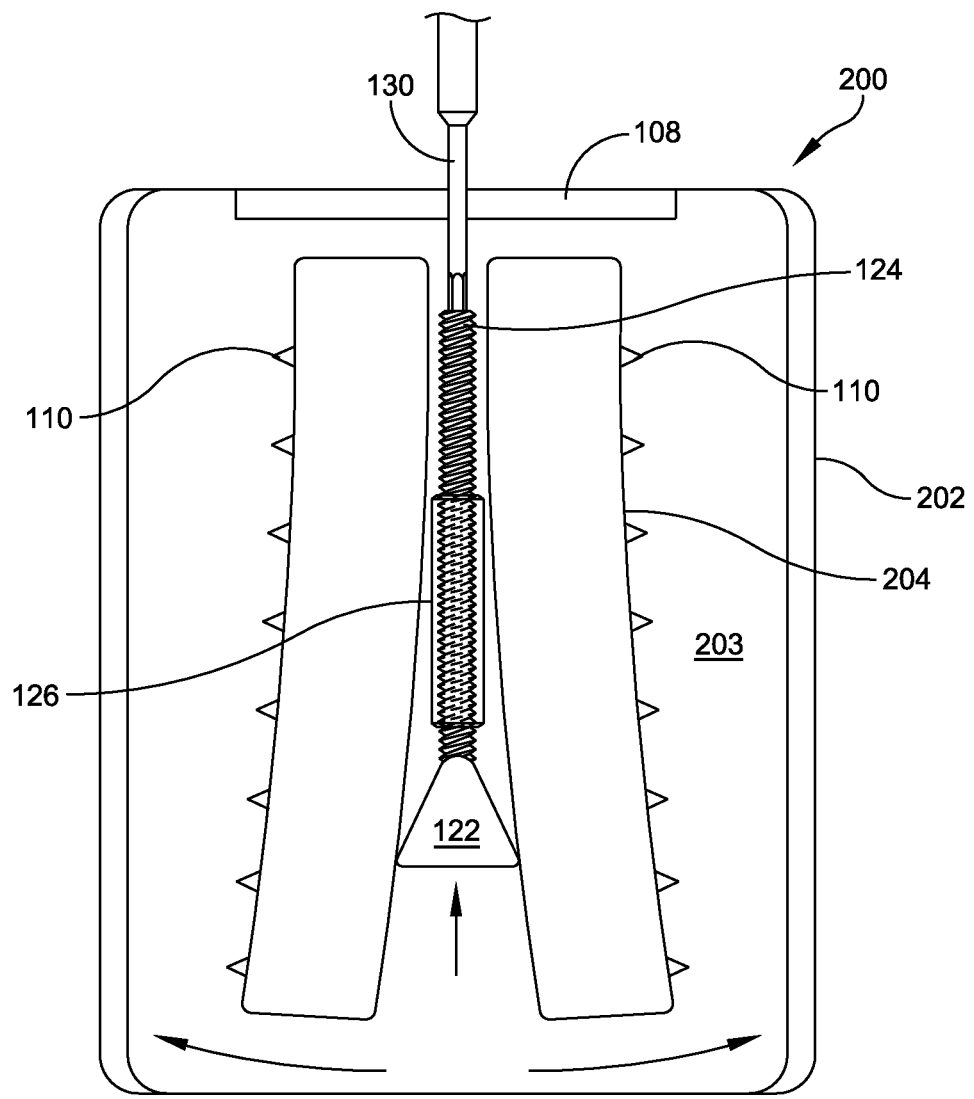
FIG. 8 is a distal (bottom) plan view of a second embodiment of the attachment plate with its arms flexed.
Figure 9:
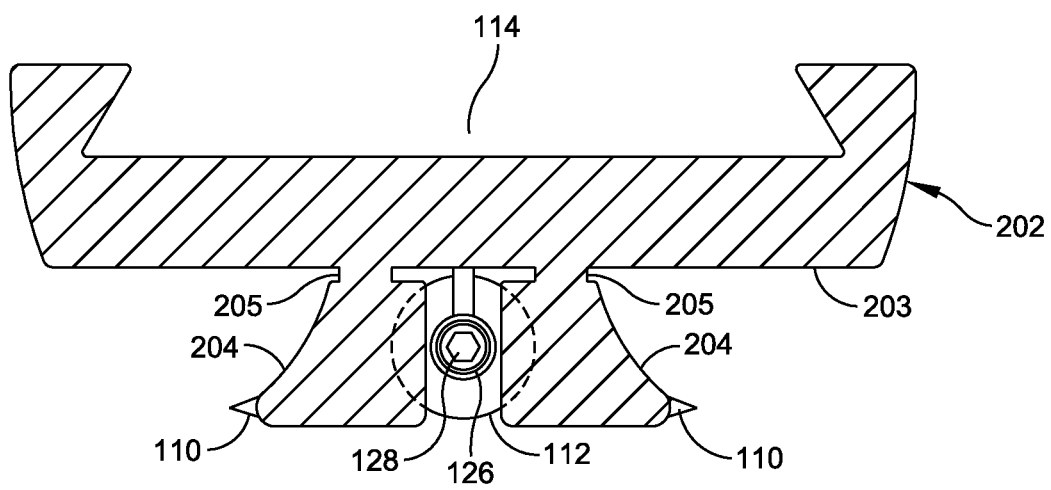
FIG. 9 is a cross section of the attachment plate of FIG. 8.

FIGS. 8 and 9 show a second embodiment of the attachment plate, in which each of the arms 204 is fixedly attached at one end (e.g., the anterior end) to the second (attachment) surface 203 of the talar component 140 by an integral post 205 joining each respective arm 204 to the second surface. In some embodiments, the integral posts 205 can be unitary posts formed of the same piece of material as the arms 204. The posts can have the same shape as the pins 106, but do not pivot. Thus, the anterior ends of each arm 204 are constrained. When the separator 122 is advanced in the anterior direction, the arms 204 flex in the medial and lateral directions, as shown in FIG. 8. The plate 202, arms 204 and posts 205 can be formed from a single piece of material by casting, for example.

In some embodiments, the amount of flexing of the arms 204 is small, so that the curved tracks 112 and guides 116 of the attachment plate 100 are omitted.

In another embodiment (not shown), instead of a unitary post 205, the anterior end of each arm 204 can be fixed to the plate portion 202 with two or more fasteners (e.g., screws), for greater strength. The arms 204 attached by fasteners can flex in the same manner shown in FIG. 8.

Although the operation of the pivoting arms 104 and the flexing arms 204 is similar, the pivoting arms can provide a greater expansion in the medial-lateral direction. The flexing arms 204 of FIGS. 8 and 9 can be used where less expansion is suitable, such as for hard bones, such as bones of osteoarthritis patients. The flexing arms 204 of FIGS. 8 and 9 may also be used where the arms can provide bi-cortical gripping. The pivoting arms of FIGS. 1-7 provide greater expansion, and may be suitable for softer bones, such as bones of rheumatoid arthritic patients.

Although the examples have been describe d with respect to use in the talar component 140 of an ankle prosthesis 150, the attachment mechanism and method described herein can be used for other implants. For example, the attachment mechanism and method can be used for the tibial component 160 of the ankle prosthesis 150. The plate portion 102 (or 202) can be oriented with the arms 104 (204) facing in the proximal direction, towards the tibia. A trapezoidal slot with undercut sides is formed in a resectioned distal surface of the tibia. The plate portion 102 (or 202) is attached to the tibia in the same manner described above with reference to attachment to the talus. In some embodiments, the tibial component is unitary, and further includes an articulating surface. In other embodiments, a distal portion of the tibial component having an articulating surface can be attached to the distal side of the plate portion 102 (or 202), to complete the tibial component.

Thus, in some embodiments, a prosthesis includes a first component 160 configured for attachment to a first bone of a person, the first component having an articulating surface 15; and a second component 140 having an articulating surface 27 configured for facing the articulating surface 15 of the first component 140. The second component 140 has a second surface 103 configured for facing a second bone of the person. The second surface 103 has first and second arms 104 attached thereto, for pivoting or flexing outwardly in medial and lateral directions, respectively, to engage side surfaces of a previously formed slot 21 in the second bone. The pivoting or flexing is in a plane parallel to the second surface 103.

Although the subject matter has been described in terms of exemplary embodiments, it is not limited thereto. Rather, the appended claims should be construed broadly, to include other variants and embodiments, which may be made by those skilled in the art.

What is claimed is:

1. A method of fixing an implant to a talus bone, comprising:
    forming a dovetail-shaped slot in the talus bone, the dovetail-shaped slot having opposing non-parallel sides;
    positioning a surface, a first pivot pin, and a second pivot pin of the implant adjacent the talus bone, so that pivotally attached first and second arms of the implant fit within the dovetail-shaped slot, the first and second arms being pivotally attached to the implant via the first and second pivot pins, respectively; and
    pivoting the first and second arms outwardly about the respective first and second pivot pins and toward respective side edges of the dovetail-shaped slot so as to grip cancellous bone, a posterior cortical wall, and at least one of a medial and a lateral cortical wall; wherein the first and second pivot pins are disposed on respective proximal ends of the first and second arms; and wherein pivoting the first and second arms outwardly about the respective first and second pivot pins further comprises guiding distal ends of the first and second arms outwardly via third and fourth pins that travel within slots disposed in the surface of the implant, the third pin disposed on the distal end of the first arm, and the fourth pin disposed on the distal end of the second arm.

2. The method of claim 1, wherein the step of pivoting comprises advancing a wedge between an end of the first arm and an adjacent end of the second arm, and spaced away from the first and second pivot pins.

3. The method of claim 2, wherein the step of advancing the wedge includes rotating a threaded member attached to the wedge so as to draw the wedge between the first and the second arms and towards the first and second pivot pins.

4. The method of claim 1, wherein the dovetail-shaped slot is formed with an undercut, and each of the arms has a medial-lateral dimension that increases from a proximal side of each arm adjacent the surface to a distal side of each arm opposite the proximal side thereof.

5. The method of claim 1, wherein:
    the dovetail-shaped slot is formed in cancellous bone, a respective lateral edge of each arm has a plurality of barbs, and
    the pivoting step drives the barbs into the cancellous bone.

6. The method of claim 1, further comprises positioning, after forming the dovetail-shaped slot, the first and second arms within the dovetail-shaped slot.

* * * * *